United States Patent
Liu et al.

(10) Patent No.: US 10,131,889 B1
(45) Date of Patent: Nov. 20, 2018

(54) ***CANDIDA ANTARCTICA* LIPASE B MUTANT, AND METHODS FOR MAKING AND USING THE SAME**

(71) Applicants: Liming Liu, Wuxi (CN); Bin Yang, Wuxi (CN)

(72) Inventors: Liming Liu, Wuxi (CN); Bin Yang, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 0 days.

(21) Appl. No.: 15/810,007

(22) Filed: Nov. 11, 2017

(30) Foreign Application Priority Data

Jul. 14, 2017 (CN) .......................... 2017 1 0573578

(51) Int. Cl.
*C12N 9/20* (2006.01)
*C12N 15/74* (2006.01)
*C12N 15/00* (2006.01)
*C12P 9/00* (2006.01)

(52) U.S. Cl.
CPC ................ *C12N 9/20* (2013.01); *C12P 9/00* (2013.01); *C12Y 301/01003* (2013.01)

(58) Field of Classification Search
CPC ... C12P 7/62; C12P 41/00; C12N 9/20; C12N 15/00; C12N 15/74
See application file for complete search history.

(56) References Cited

FOREIGN PATENT DOCUMENTS

| CN | 102660517 | * | 9/2012 |
| CN | 104745550 | * | 7/2015 |
| WO | 106546 | * | 9/2011 |

* cited by examiner

*Primary Examiner* — Maryam Monshipouri
(74) *Attorney, Agent, or Firm* — Lili Chen

(57) ABSTRACT

The present invention relates to the field of bioengineering. It provides a *Candida antarctica* lipase B mutant and its application. The mutant enzyme overcomes the limit of the parent enzyme that can exhibit high enantioselectivity towards (R)-3-TBDMSO glutaric acid methyl monoester only at temperatures below 5° C. The mutant enzyme successfully increased R-ee value at 5-70° C. The mutant D223V/A281S exhibits high R-ee value (>99%), high conversion rate (80%), and high space-time yield (107.54 g $L^{-1}$ $d^{-1}$). The present invention lays a foundation for industrial production of (R)-3-TBDMSO glutaric acid methyl monoester using a biosynthesis approach and provide insights into conformational dynamics-based enzyme design.

9 Claims, 3 Drawing Sheets
Specification includes a Sequence Listing.

SEQUENCE LISTING

```
<160> NUMBER OF SEQ ID NOS: 17

<210> SEQ ID NO 1
<211> LENGTH: 317
<212> TYPE: PRT
<213> ORGANISM: Unknown
<220> FEATURE:
<223> OTHER INFORMATION: Synthetic Sequence

<400> SEQUENCE: 1

Leu Pro Ser Gly Ser Asp Pro Ala Phe Ser Gln Pro Lys Ser Val Leu
1               5                   10                  15

Asp Ala Gly Leu Thr Cys Gln Gly Thr Ser Pro Thr Ser Val Thr Lys
            20                  25                  30

Pro Ile Leu Leu Val Pro Gly Thr Gly Thr Thr Gly Pro Gly Lys Phe
        35                  40                  45

Asp Ser Asn Trp Ile Pro Leu Ser Thr Gln Leu Gly Tyr Thr Pro Cys
    50                  55                  60

Trp Ile Ser Pro Pro Phe Met Leu Asn Asp Thr Gln Val Asn Thr
65                  70                  75                  80

Glu Tyr Met Val Asn Ala Ile Thr Thr Leu Tyr Ala Gly Ser Gly Asn
                85                  90                  95

Arg Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Ser Val Leu Ser Gly Pro Leu
    130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
            180                 185                 190

Gln Val Ser Asn Ser Pro Leu Asp Asp Ser Tyr Leu Phe Asn Gly Lys
        195                 200                 205

Asn Val Gln Ala Gln Ala Val Cys Gly Pro Leu Phe Val Ile Asp His
    210                 215                 220

Ala Gly Ser Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Val Ala Ile Ile Ala Gly
        275                 280                 285
```

```
Pro Lys Gln Asn Cys Glu Pro Asp Leu Met Pro Tyr Ala Arg Pro Phe
    290                 295                 300

Ala Val Gly Lys Arg Thr Cys Ser Gly Ile Val Thr Pro
305                 310                 315

<210> SEQ ID NO 2
<211> LENGTH: 951
<212> TYPE: DNA
<213> ORGANISM: Unknown
<220> FEATURE:
<223> OTHER INFORMATION: Synthetic Sequence

<400> SEQUENCE: 2
ctaccttccg gttcggaccc tgccttctcc cagcccaaat ccgtcctcga cgccggccta      60
acctgccaag gcacctctcc tacctccgtg accaaaccca tcctcctcgt gcccggaaca     120
ggcaccacgg gtccgggaaa gttcgactcg aactggatcc cgctctctac gcagcttggc    180
tacacaccgt gctggatctc accgccgccg ttcatgctca acgacacgca ggtcaacacc    240
gaatacatgg tcaacgccat caccacactc tacgccggtt cgggcaatcg aaagcttcct    300
gtgcttacgt ggtctcaagg tgggctggtg gcacagtggg gtttgacctt cttccccagt    360
atcaggtcca aggtcgatcg acttatggcc tttgcgcccg actacaaggg ctccgtcctc    420
tccggccctc tcgatgcact cgcggttagt gcaccctccg tatggcagca aaccaccggt    480
tcggcactca ccaccgcact ccgaaacgca ggtggtctga cccagatcgt gcccaccacc    540
aacctctact cggccaccga cgagatcgtt cagccccagg tgtccaactc gcccctcgac    600
tcgtcgtacc tcttcaacgg aaagaacgtc caggcacagg cagtttgtgg cccgctgttt    660
gtgattgtcc atgcgggatc gctcacctcg cagttctcct acgtcgtcgg tcgatccgcc    720
ctgcgctcca ccacgggcca ggctcgtagt gccgactacg gaatcacgga ctgcaaccct    780
cttcctgcaa atgatctgac ccccgagcaa aaggtcgccg cggcagcgct gctcgcccct    840
gcggctgtgg ccatcatcgc gggtccaaag cagaactgcg aacccgacct catgccctac    900
gcccgcccct tgccgtcgg caagaggacc tgctccggca tcgtcacccc c              951

<210> SEQ ID NO 3
<211> LENGTH: 951
<212> TYPE: DNA
<213> ORGANISM: unknown
<220> FEATURE:
<223> OTHER INFORMATION: Synthetic sequence

<400> SEQUENCE: 3
ctaccttccg gttcggaccc tgccttctcc cagcccaaat ccgtcctcga cgccggccta      60
acctgccaag gcacctctcc tacctccgtg accaaaccca tcctcctcgt gcccggaaca     120
ggcaccacgg gtccgggaaa gttcgactcg aactggatcc cgctctctac gcagcttggc    180
tacacaccgt gctggatctc accgccgccg ttcatgctca acgacacgca ggtcaacacc    240
gaatacatgg tcaacgccat caccacactc tacgccggtt cgggcaatcg aaagcttcct    300
gtgcttacgt ggtctcaagg tgggctggtg gcacagtggg gtttgacctt cttccccagt    360
atcaggtcca aggtcgatcg acttatggcc tttgcgcccg actacaaggg ctccgtcctc    420
tccggccctc tcgatgcact cgcggttagt gcaccctccg tatggcagca aaccaccggt    480
tcggcactca ccaccgcact ccgaaacgca ggtggtctga cccagatcgt gcccaccacc    540
aacctctact cggccaccga cgagatcgtt cagccccagg tgtccaactc gcccctcgac    600
tcgtcgtacc tcttcaacgg aaagaacgtc caggcacagg cagtttgtgg cccgctgttt    660
```

```
gtgattgacc atgcgggatc gctcacctcg cagttctcct acgtcgtcgg tcgatccgcc    720
ctgcgctcca ccacgggcca ggctcgtagt gccgactacg gaatcacgga ctgcaaccct    780
cttcctgcaa atgatctgac ccccgagcaa aaggtcgccg cggcagcgct gctcgcccct    840
tcggctgtgg ccatcatcgc gggtccaaag cagaactgcg aacccgacct catgccctac    900
gcccgcccct tgccgtcgg caagaggacc tgctccggca tcgtcacccc c              951
```

<210> SEQ ID NO 4
<211> LENGTH: 951
<212> TYPE: DNA
<213> ORGANISM: unknown
<220> FEATURE:
<223> OTHER INFORMATION: Synthetic sequence

<400> SEQUENCE: 4

```
ctaccttccg gttcggaccc tgccttctcc cagcccaaat ccgtcctcga cgccggccta     60
acctgccaag gcacctctcc tacctccgtg accaaaccca tcctcctcgt gcccggaaca    120
ggcaccacgg gtccgggaaa gttcgactcg aactggatcc cgctctctac gcagcttggc    180
tacacaccgt gctggatctc accgccgccg ttcatgctca acgacacgca ggtcaacacc    240
gaatacatgg tcaacgccat caccacactc tacgccggtt cgggcaatcg aaagcttcct    300
gtgcttacgt ggtctcaagg tgggctggtg gcacagtggg gtttgacctt cttccccagt    360
atcaggtcca aggtcgatcg acttatggcc tttgcgcccg actacaaggg ctccgtcctc    420
tccggccctc tcgatgcact cgcggttagt gcaccctccg tatggcagca aaccaccggt    480
tcggcactca ccaccgcact ccgaaacgca ggtggtctga cccagatcgt gcccaccacc    540
aacctctact cggccaccga cgagatcgtt cagccccagg tgtccaactc gccccctcgac   600 tcgtcgtacc tcttcaacgg aaagaacgtc caggcacagg cagtttgtgg cccgctgttt    660
gtgattgtcc atgcgggatc gctcacctcg cagttctcct acgtcgtcgg tcgatccgcc    720
ctgcgctcca ccacgggcca ggctcgtagt gccgactacg gaatcacgga ctgcaaccct    780
cttcctgcaa atgatctgac ccccgagcaa aaggtcgccg cggcagcgct gctcgcccct    840
tcggctgtgg ccatcatcgc gggtccaaag cagaactgcg aacccgacct catgccctac    900
gcccgcccct tgccgtcgg caagaggacc tgctccggca tcgtcacccc c              951
```

<210> SEQ ID NO 5
<211> LENGTH: 28
<212> TYPE: DNA
<213> ORGANISM: unknown
<220> FEATURE:
<223> OTHER INFORMATION: DNA primer

<400> SEQUENCE: 5

```
ctgtttgtca ttgtccatgc gggatcgc                                        28
```

<210> SEQ ID NO 6
<211> LENGTH: 28
<212> TYPE: DNA
<213> ORGANISM: unknown
<220> FEATURE:
<223> OTHER INFORMATION: DNA primer

<400> SEQUENCE: 6

```
gcgatcccgc atggacaatc acaaacag                                        28
```

<210> SEQ ID NO 7

```
<211> LENGTH: 25
<212> TYPE: DNA
<213> ORGANISM: unknown
<220> FEATURE:
<223> OTHER INFORMATION: DNA primer

<400> SEQUENCE: 7
ctgctcgccc cttcggctgt ggcca                                              25

<210> SEQ ID NO 8
<211> LENGTH: 25
<212> TYPE: DNA
<213> ORGANISM: unknown
<220> FEATURE:
<223> OTHER INFORMATION: DNA primer

<400> SEQUENCE: 8
tggccacagc cgaaggggcg agcag                                              25

<210> SEQ ID NO 9
<211> LENGTH: 25
<212> TYPE: DNA
<213> ORGANISM: unknown
<220> FEATURE:
<223> OTHER INFORMATION: DNA primer

<400> SEQUENCE: 9
ctcgcccctg cgtctgtggc catca                                              25

<210> SEQ ID NO 10
<211> LENGTH: 25
<212> TYPE: DNA
<213> ORGANISM: unknown
<220> FEATURE:
<223> OTHER INFORMATION: DNA primer

<400> SEQUENCE: 10
tgatggccac agacgcaggg gcgag                                              25

<210> SEQ ID NO 11
<211> LENGTH: 28
<212> TYPE: DNA
<213> ORGANISM: unknown
<220> FEATURE:
<223> OTHER INFORMATION: DNA primer

<400> SEQUENCE: 11
ctgtgcttac ggcgtctcaa ggtgggct                                           28

<210> SEQ ID NO 12
<211> LENGTH: 28
<212> TYPE: DNA
<213> ORGANISM: unknown
<220> FEATURE:
<223> OTHER INFORMATION: DNA primer

<400> SEQUENCE: 12
agcccacctt gagacgccgt aagcacag                                           28

<210> SEQ ID NO 13
<211> LENGTH: 34
<212> TYPE: DNA
<213> ORGANISM: unknown
<220> FEATURE:
<223> OTHER INFORMATION: DNA primer

<400> SEQUENCE: 13
```

-continued accctccgta tggcagaata ccaccggttc gtgt                                34

<210> SEQ ID NO 14
<211> LENGTH: 34
<212> TYPE: DNA
<213> ORGANISM: unknown
<220> FEATURE:
<223> OTHER INFORMATION: DNA primer

<400> SEQUENCE: 14
acacgaaccg gtggtattct gccatacgga gggt                                34

<210> SEQ ID NO 15
<211> LENGTH: 317
<212> TYPE: PRT
<213> ORGANISM: Unknown
<220> FEATURE:
<223> OTHER INFORMATION: synthetic sequence

<400> SEQUENCE: 15

Leu Pro Ser Gly Ser Asp Pro Ala Phe Ser Gln Pro Lys Ser Val Leu
1               5                   10                  15

Asp Ala Gly Leu Thr Cys Gln Gly Thr Ser Pro Thr Ser Val Thr Lys
            20                  25                  30

Pro Ile Leu Leu Val Pro Gly Thr Gly Thr Thr Gly Pro Gly Lys Phe
        35                  40                  45

Asp Ser Asn Trp Ile Pro Leu Ser Thr Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Thr Leu Tyr Ala Gly Ser Gly Asn
                85                  90                  95

Arg Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Ser Val Leu Ser Gly Pro Leu
    130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
            180                 185                 190

Gln Val Ser Asn Ser Pro Leu Asp Asp Ser Tyr Leu Phe Asn Gly Lys
        195                 200                 205

Asn Val Gln Ala Gln Ala Val Cys Gly Pro Leu Phe Val Ile Val His
    210                 215                 220

Ala Gly Ser Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Val Ala Ile Ile Ala Gly
        275                 280                 285

Pro Lys Gln Asn Cys Glu Pro Asp Leu Met Pro Tyr Ala Arg Pro Phe
290                 295                 300

Ala Val Gly Lys Arg Thr Cys Ser Gly Ile Val Thr Pro
305                 310                 315

<210> SEQ ID NO 16
<211> LENGTH: 317
<212> TYPE: PRT
<213> ORGANISM: Unknown
<220> FEATURE:
<223> OTHER INFORMATION: synthetic sequence

<400> SEQUENCE: 16

Leu Pro Ser Gly Ser Asp Pro Ala Phe Ser Gln Pro Lys Ser Val Leu
1               5                   10                  15

Asp Ala Gly Leu Thr Cys Gln Gly Thr Ser Pro Thr Ser Val Thr Lys
                20                  25                  30

Pro Ile Leu Leu Val Pro Gly Thr Gly Thr Thr Gly Pro Gly Lys Phe
            35                  40                  45

Asp Ser Asn Trp Ile Pro Leu Ser Thr Gln Leu Gly Tyr Thr Pro Cys
        50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Thr Leu Tyr Ala Gly Ser Gly Asn
                85                  90                  95

Arg Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Ser Val Leu Ser Gly Pro Leu
130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
            180                 185                 190

Gln Val Ser Asn Ser Pro Leu Asp Asp Ser Tyr Leu Phe Asn Gly Lys
        195                 200                 205

Asn Val Gln Ala Gln Ala Val Cys Gly Pro Leu Phe Val Ile Asp His
210                 215                 220

Ala Gly Ser Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ser Ala Val Ala Ile Ile Ala Gly
        275                 280                 285

Pro Lys Gln Asn Cys Glu Pro Asp Leu Met Pro Tyr Ala Arg Pro Phe
290                 295                 300

Ala Val Gly Lys Arg Thr Cys Ser Gly Ile Val Thr Pro
305                 310                 315

<210> SEQ ID NO 17
<211> LENGTH: 317

-continued

```
<212> TYPE: PRT
<213> ORGANISM: Unknown
<220> FEATURE:
<223> OTHER INFORMATION: synthetic sequence

<400> SEQUENCE: 17

Leu Pro Ser Gly Ser Asp Pro Ala Phe Ser Gln Pro Lys Ser Val Leu
1               5                   10                  15

Asp Ala Gly Leu Thr Cys Gln Gly Thr Ser Pro Thr Ser Val Thr Lys
            20                  25                  30

Pro Ile Leu Leu Val Pro Gly Thr Gly Thr Thr Gly Pro Gly Lys Phe
        35                  40                  45

Asp Ser Asn Trp Ile Pro Leu Ser Thr Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Thr Leu Tyr Ala Gly Ser Gly Asn
                85                  90                  95

Arg Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Ser Val Leu Ser Gly Pro Leu
    130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
            180                 185                 190

Gln Val Ser Asn Ser Pro Leu Asp Asp Ser Tyr Leu Phe Asn Gly Lys
        195                 200                 205

Asn Val Gln Ala Gln Ala Val Cys Gly Pro Leu Phe Val Ile Val His
    210                 215                 220

Ala Gly Ser Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ser Ala Val Ala Ile Ile Ala Gly
        275                 280                 285

Pro Lys Gln Asn Cys Glu Pro Asp Leu Met Pro Tyr Ala Arg Pro Phe
    290                 295                 300

Ala Val Gly Lys Arg Thr Cys Ser Gly Ile Val Thr Pro
305                 310                 315
```

CANDIDA ANTARCTICA LIPASE B MUTANT, AND METHODS FOR MAKING AND USING THE SAME

CROSS-REFERENCES AND RELATED APPLICATIONS

This application claims the benefit of priority to Chinese Application No. 201710573578.X, entitled "A *Candida antarctica* lipase B mutant, and methods for making and using the same", filed Jul. 14, 2017, which is herein incorporated by reference in its entirety.

BACKGROUND OF THE INVENTION

Field of the Invention

The present invention relates to the field of bioengineering, and more particularly relates to a *candida antarctica* lipase B mutant and its application.

Description of the Related Art

Optically pure (R)-3-substituted glutaric acid monoesters (R-$J_6$) are important building blocks for the synthesis of many pharmaceutically important compounds such as pitavastatin, fluvastatin, atorvastatin, and rosuvastatin. Among these, rosuvastatin inhibits hydroxymethylglutaryl-CoA reductase and has few side-effects. R-$J_6$ can be obtained by four approaches: chemical synthesis, hydrolysis of dialkyl-3-substituted glutaric acids by using hydrolases, kinetic resolution of racemates, and desymmetrization of prochiral compounds. To date, industrial (R)-$J_6$ is mainly prepared by chemical synthesis. (S)-1-phenethylamin is used to catalyze the asymmetric reduction of 3-substituted glutaric acid monoesters, with a space-time yield of 13.6 g $L^{-1}$ $h^{-1}$, a low yield (54.9%), and a low enantiomeric excess (R-ee; 80%) at −78° C. Biocatalysis method provides an attractive alternative to chemical synthesis and it is environmentally friendly. R, S-$J_6$ may be prepared by using pig liver esterase and Novozym 435. Although the space-time yield of such a reaction is high (>4.5 g $L^{-1}$ $h^{-1}$), the selectivity for the (R)-isomer is low. α-Chymotrypsin is also employed in R-$J_6$ preparation, which hydrolyzes the dialkyl-3-substituted glutaric acid with a high R-ee of 97%. This approach comprises six steps, starting from diethyl-3-t-butyl-dimethyl-silyloxy (TBDMSO) glutaric acid (conversion rate, 65.4%; isolated yield, 53.2%), and the 3-substituent group of the substrate significantly affects the catalytic efficiency and enantioselectivity.

*Candida antarctica* Lipase B (CALB; EC 3.1.1.3), a member of α/β-hydrolase family, possesses the catalytic triad Ser105-Asp187-His224 which lies between the two binding pockets (the acyl binding pocket and the alcohol binding pocket) and is widely used in both academic and industrial production. A conserved sequence of Thr-X-Ser-X-Gly is in the vicinity of the active site of CALB, and the activity center of CALB doesn't have spiral fragments buried compared with other lipases, therefore, CALB doesn't have interface activity.

Enzymes with high enantioselectivity have been widely used as biocatalysts to produce optically pure valuable compounds in recent years. However, in many cases, enzymes exhibit satisfactory enantioselectivity only at low temperatures (even down to −80° C.), with decreasing enantioselectivity at higher temperatures. Thus, low-temperature methods have been applied to improve the enantioselectivity of enzymes. Although great efforts have been made to increase reaction rates at low temperatures to some extent, such as using the immobilized enzymes on porous ceramics, the high costs and low yields associated with low temperatures remain a limiting factor for its industrial applications. It has been shown that the attempt to maintain satisfactory enantioselectivity for enzymes at higher temperature through protein engineering is plausible, but simple and accurate strategies for protein engineering warrant further discussion.

Recently, there has been growing interest in the conformational dynamics of proteins, which plays an important role in enzyme catalysis. The engineering of the conformational dynamics of enzymes has become an effective strategy for protein design and has achieved significant progress in terms of relieving product inhibition and the rational design of enzymes. Recent studies have also indicated that the conformational dynamics of proteins, which are crucial for ligand recognition and binding, may determine ligand-binding orientations and thereby be responsible for selectivity. Despite the fact that there has been no direct report on the relationship between the conformational dynamics and the enantioselectivity of an enzyme, engineering of the conformational dynamics of an enzyme is expected to provide informative guidance on improving enantioselectivity.

Based on our previous research, the preparation of (R)-3-TBDMSO from 3-t-butyl-dimethyl-silyloxy (TBDMSO) can be achieved by using CALB, however its enantioselectivity is poor, and its enantioselectivity of wild type is S configuration. We have obtained a mutant CALB named EF5 whose activity pocket was modified by protein engineering. The R-ee of this mutant is 98.5% under 5° C., and its R-ee decreases with increasing reaction temperature. The industrial application of EF5 was hampered because it requires the largely extended production cycle and the high cost due to low temperature (<5° C.) requirement. There is a need to further modify CALB EF5 to achieve high R-ee under higher temperatures.

DETAILED DESCRIPTION

To solve the above problems, the invention provides a *candida antarctica* lipase B mutant, a construction method thereof, and its application in preparing (R)-3-t-butyl-dimethyl-silyloxy (TBDMSO) glutaric acid methyl monoester at higher temperature (20-55° C.), rather than at 5° C. The method, which has high productivity, high enantioselectivity and low production cost, has great potential in industrial applications.

The first goal of the present invention is to provide a *candida antarctica* lipase B mutant, which has one of the following amino acid substitutions: D223V, A281S or D223V/A281S as compared to the parent enzyme, CALB EF5, having an amino acid sequence of SEQ ID NO:1.

In one embodiment of the present invention, the nucleotide sequences of the mutant D223V, A281S and D223V/A281S are set forth in SEQ ID NO:2, SEQ ID NO:3, and SEQ ID NO:4, respectively.

In one embodiment of the present invention, the amino acid sequences of the mutant D223V, A281S and D223V/A281S are set forth in SEQ ID NO:15, SEQ ID NO:16, and SEQ ID NO: 17, respectively.

The second goal of the present invention is to provide a method for obtaining the lipase mutant, comprising the following steps:

1) selecting candidate mutation residues based on structural analysis of the parent enzyme, CALB EF5;

2) identifying key residues for mutation based on molecular dynamics (MD) simulations: performing MD simulations for alanine or serine substitutions of each candidate mutation residue, calculating the root-mean-square fluctuation (RMSF) of α-carbons for each substitution, and choosing the mutation that leads to reduction of the RMSF of the active site of the enzyme.

3) constructing a recombinant plasmid comprising a gene encoding a mutant enzyme with above-identified mutations, wherein the mutant gene is generated from a PCR using a mutant oligonucleotide as the primer and CALB EF5 parent gene as the template;

4) constructing a recombinant strain by transforming the recombinant plasmid into an expression host cell;

5) obtaining the *candida antarctica* lipase B mutant by expressing the mutant lipase B from the cultivated recombinant strain carrying the mutant lipase gene.

The third goal of the present invention is to provide a recombinant plasmid comprising a gene that encodes the mutant lipase B.

The present invention also provides a recombinant strain expressing the mutant lipase B.

In one embodiment of the present invention, the recombinant strain is constructed from expression host *Pichia pastoris* GS115.

The present invention also provides a method of using the mutant lipase B to prepare (R)-3-substituted glutaric acid alkyl monoester compounds.

The present invention also provides a method of using the mutant lipase B to prepare (R)-3-t-butyl-dimethyl-silyloxy glutaric acid methyl monoester.

In one embodiment, the present invention provides a method of preparing 3-substituted glutaric acid monoester, comprising mixing substrate, co-substrate, mutant enzyme of the invention in organic solvent in a non-aqueous phase catalytic reaction, wherein the molar ratio of substrate to co-substrate is 1:20-20:1; the mass ratio of substrate to enzyme is 1:6-6:1; the molar ratio of organic solvent to substrate is 2:1-300:1; and wherein the substrate is 3-substituted glutaric anhydride or 3-substituted glutaric acid and the co-substrate is organic alcohol.

In one embodiment of the present invention, the organic solvent is one or more solvents selected from a group consisting of MTBE, acetonitrile, and tetrahydrofuran.

In one embodiment of the present invention, the organic alcohol is one or more alcohols selected from a group consisting of methanol, ethanol, propanol, isopropanol, n-butanol, 2-butanol and tert butanol.

In one embodiment of the present invention, 0.5% v/v metal ion solution is added to the reaction system wherein the metal ion solution is $MgCl_2$, $CaCl_2$ or KCl.

In one embodiment of the present invention, the reaction is performed with enzyme concentration of 1 to 100 g/L and substrate concentration of 10 to 300 g/L under the condition of 5-70° C., 200-500 rpm for 2-48 hr.

In one embodiment of the present invention, the reaction is performed with enzyme concentration of 1 to 100 g/L and substrate concentration of 10 to 300 g/L under the condition of 10-55° C., 200-500 rpm for 2-48 hr.

In one embodiment of the present invention, the reaction temperature is 37° C. and the reaction time is 12 hr.

In one embodiment of the present invention, the enzyme is an immobilized enzyme or a free enzyme.

In one embodiment of the present invention, the fixed media of the immobilized enzyme is diatomite, sodium alginate, kaolin, agarose, gelatin, cation resin, anion resin or macroporous adsorption resin.

The present invention also provides the application of the mutant lipase in pharmaceutical manufacturing of medically active compounds.

Nomenclature for amino acid modifications in the present invention is explained in detail as follows.

The mutated amino acid in the mutant is marked as "original amino acid, position, substituted amino acids". For example, D223V indicates a substitution of Asp at the position 223 with Val. The position number indicates to the amino acid location in the parent lipase with an amino sequence of SEQ NO.1. D223V/A281S indicates the position of 223 and 281 are both mutated.

The present invention provides CALB mutants that can catalyze reactions to produce (R)-3-TBDMSO glutaric acid methyl monoester with high enantioselecitivity towards R-products at room temperature and other industrialized acceptable temperatures. The mutant enzymes exhibit high enantioselecitivity at 5-70° C. with decreased reaction time, increased reaction efficiency and decreased production cost as compared to those of the parent enzyme. High yield (80%) and high R-ee (>99%) of (R)-3-TBDMSO glutaric acid methyl monoester production was achieved using the mutant enzyme of the invention. The mutant enzyme of the invention overcame the limit of the parent enzyme (CALB-EF5) which can exhibit high enantioselectivity only at low temperatures below 5° C. The present invention lays the foundation for industrial production of (R)-3-TBDMSO glutaric acid methyl monoester.

EXAMPLES

The invention is further illustrated in more detail with reference to the accompanying examples. It is noted that, the following embodiments are only intended for purposes of illustration and are not intended to limit the scope of the invention.

Materials and Methods:

Gene source: the CALB gene was derived from *Pseudozyma antarctia* JCM 3941, which was purchased from Japan Collection of Microorganisms (JCM). The CALB mutants were obtained by molecular modification, and other chemicals and solvents (analytical grade) were obtained from local suppliers.

The analysis of conformational dynamics of CALB: performing MD simulations and calculating the RMSF of α-carbons to analyze changes of the conformational dynamics. The MD simulations were performed with the GRO- MACS 4.5.5 and the AMBER03 force field following three main steps of energy minimization, system equilibration and production protocols.

The analysis of enzyme structure and its interaction with substrate: structural analysis was performed with Pymol. Molecular docking was performed with Autodock.

Determination of R-ee value and conversion rate: the concentrations of (R)-3-TBDMSO glutaric acid methyl monoester and enantioselectivity were determined by HPLC. The mobile phase consisted of 96% hexane and 4% iso-propanol with 0.02% (v/v) trifluoroacetic acid, filtered through a 0.22 μm membrane before use. Analysis was performed by injecting a 20 μL sample into the chromatograph, with detection temperature of 25° C. and 1 mL/min flow rate; sample detection time was 15 min. The R-ee value was defined as follows: R-ee=(R−S)/(R+S)*100%, wherein R and S represent the concentrations of R and S enantiomer, respectively.

Example 1: Selection of Mutation Sites

Structural analysis: CALB EF possesses the catalytic triad Asp187-His224-Ser105 which lay between the two binding pockets (the acyl binding pocket and the alcohol binding pocket). The acyl binding pocket is mainly composed of A141, L144, V149, D134, T138 and Q157, and the alcohol binding pocket is mainly composed of T42, K47, W104, L278, A281 and A282. Residues A281, A282, and 1285 point towards alcohol moiety of substrates and limit the size of the channel.

Figure 1:
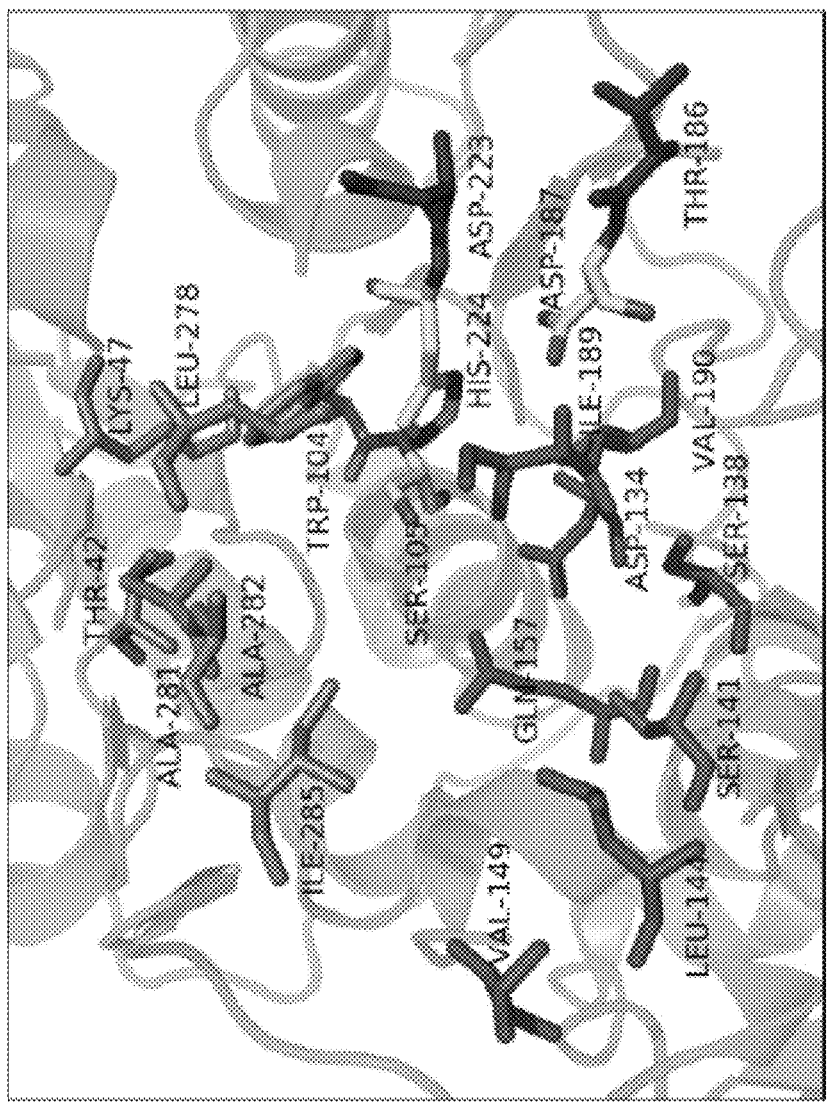
FIG. 1. The activity pocket of CALB.
Figure 2:
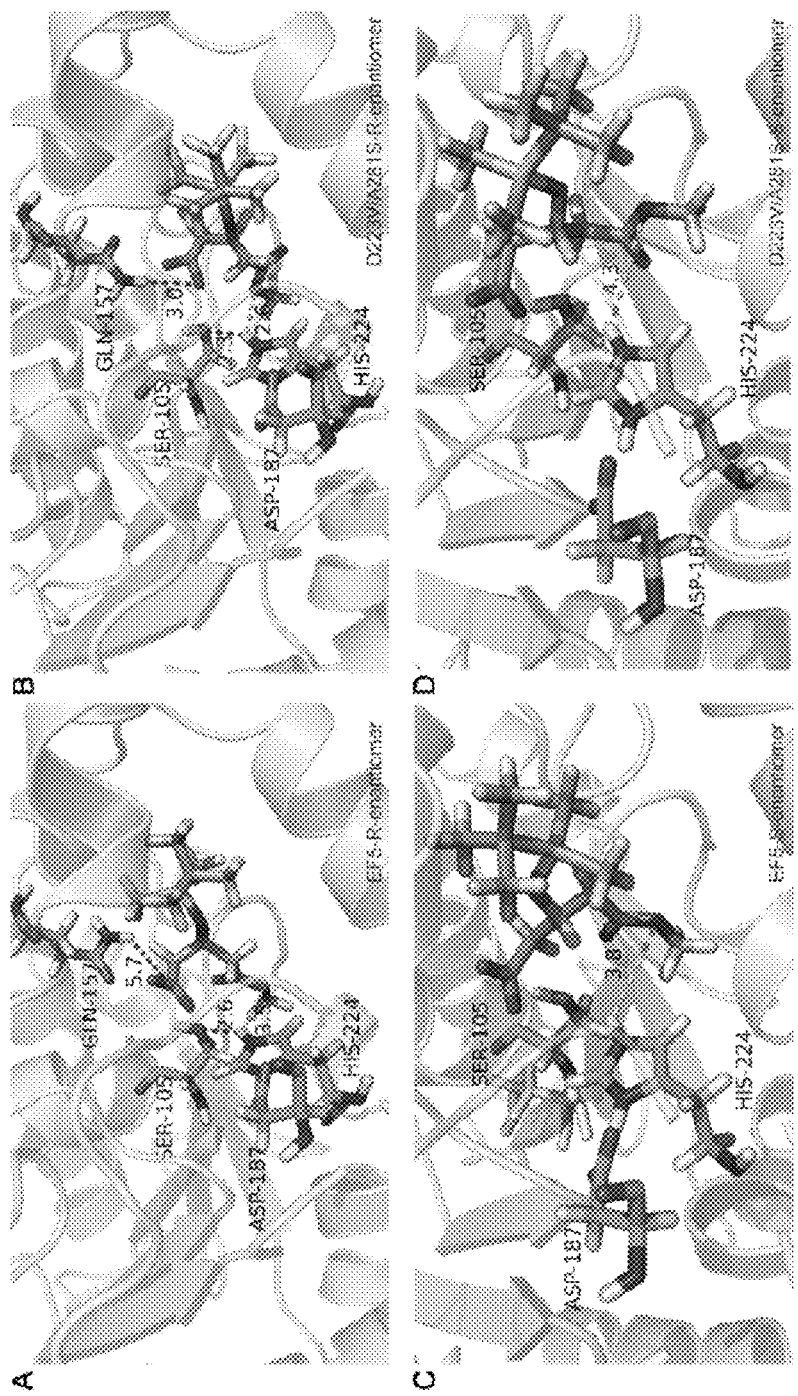
FIG. 2. Comparison of the conformational changes between R/S enantiomer-bound CALB EF5 and D223V/A281S mutant. Conformations of the activity pockets are shown in (A) R-enantiomer bound EF5; (B) R-enantiomer bound D223V/A281S mutant; (C) S-enantiomer bound EF5; and (D) S-enantiomer-bound D223V/A281S mutant.
Figure 3:
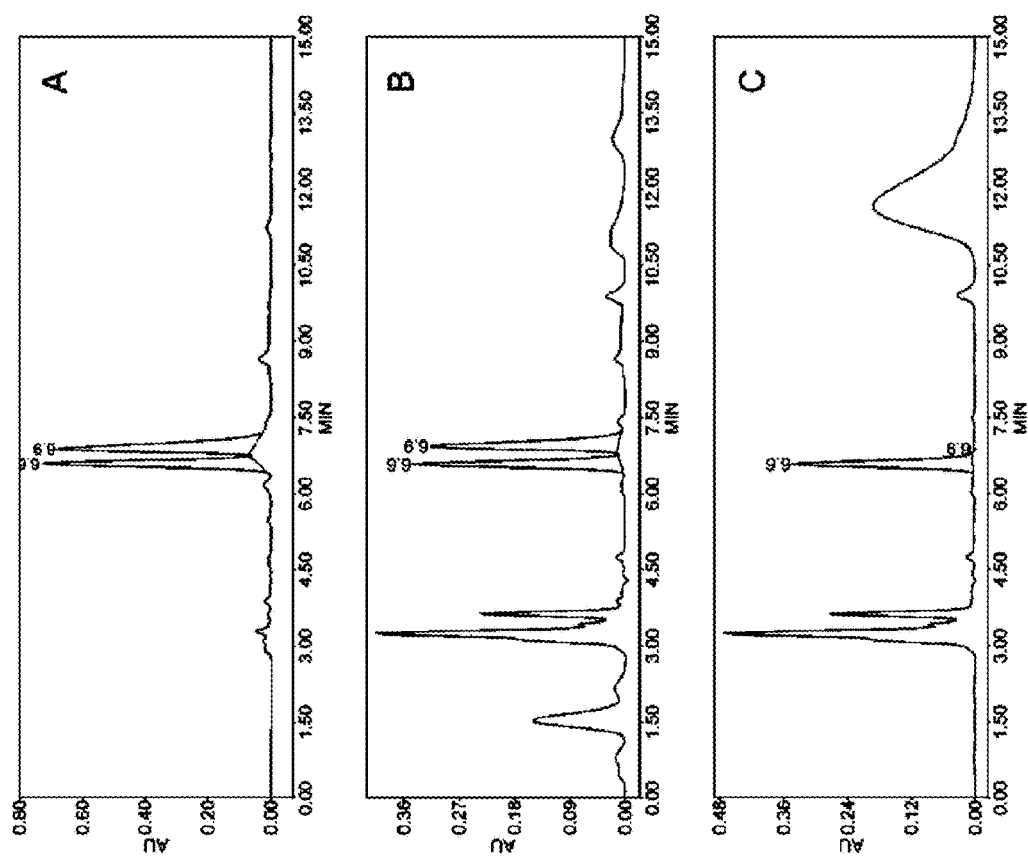
FIG. 3. HPLC analysis of the esterification catalyzed by CALB EF5 and D223V/A281S at 30° C., $T_R$=6.6 min, Ts=6.9 min. (A) Racemic 3-TBDMSO glutaric acid methyl monoester; (B) EF5-catalyzed esterification (8% R-ee, 82.17% yield); (C) D223V/A281S-catalyzed esterification (>99% R-ee, 80.25% yield).

Selection of mutation sites: six residues (D134, A148, V149, 1189, V190 and Q157) on acyl binding pocket and five residues (T42, T43, W104, A281 and A282) on alcohol binding pocket and the entrance of the channel were selected. Besides, D223 and T186, which are in front of the catalytic residues His224 and Asp187, were also selected. The residues are shown in FIG. 1.

Example 2: The Effects of Candidate Residues on Enantioselectivity

Mutant libraries of residues D134, A148, V149, 1189, V190, Q157, T42, T43, W104, A281, A282, D223 and T186, which were chosen based on the structural analysis, were constructed, and the effects of the mutants on the enantioselectivity were examined through high throughput screening. Nine combination libraries were constructed, including library 1 (A148/V149), library 2 (I189/V190), library 3 (Q157), library 4 (T42/T43), library 5 (W104), library 6 (A281/A282), library 7 (D223), library 8 (T186), library 9 (D134). Out of the 7000 mutants that were screened, only D223V, A281S and D223V/A281S mutants exhibited significant change in the R-ee value as compared to that of the parent enzyme (CALB EF5). In addition, A282S, W104A and Q157N mutants were also selected further experimental evaluation.

Example 3: Construction of CALB Mutants

Six mutants, D223V, A281S, A282S, W104A, Q157N and D223V/A281S, were successfully constructed by site directed mutagenesis using PCR. The PCR primers used for site-directed mutagenesis were shown in SEQ ID NO:5 and SEQ ID NO:6, SEQ ID NO:7 and SEQ ID NO:8, SEQ ID NO:9 and SEQ ID NO:10, SEQ ID NO:11 and SEQ ID NO:12, SEQ ID NO:13 and SEQ ID NO:14. The DNA template is a plasmid comprising a CALB EF5 parent gene.

1 μL of Dpn I (10 U μL$^{-1}$) was added to 25 μL of the PCR reaction mixture and incubated 3 hr at 37° C. to eliminate the template plasmid. The digested PCR product was inserted into pGAOZαA plasmid and transformed into *Escherichia coli* JM109 for plasmid amplification. The plasmid pGAPZαA-mutants were obtained from *E. coli* JM109 and linearized by AvrII, and were then purified and transformed into *P. pastoris* GS115. Recombinant *P. pastoris* GS115 were inoculated into yeast extract peptone dextrose (YPD) medium (10 g L$^{-1}$ of yeast extract, 20 g L$^{-1}$ of peptone, and 20 g L$^{-1}$ of glucose) and grown at 30° C. on a rotary shaker (200 rpm) for 2 days.

Example 4: Measurement of the Initial Generation Rates of R/S Enantiomers in Esterification Reactions Catalyzed by CALB Mutants For the esterification reaction, 1.23 mM 3-TBDMSO glutaric anhydride and 1.23 mM methanol were dissolved in acetonitrile (5 mL), followed by ultrasonic dispersion. Enzyme (400 mg) was then added to the reaction system. The mixed system was incubated at 30° C., 200 rpm. At appropriate times, samples were collected and analyzed by high-performance liquid chromatography (HPLC). Several data points were collected to determine the initial generation rate of each enantiomer. The activities of the immobilized mutant enzymes were maintained at the same level.

As illustrated in Table 1, the $V_S$ values of the mutants A281S, D223V, and D223V/A281S significantly decreased from 79.99±3.18 in the parent CALB-EF5 to 3.14±0.04, 2.00±0.01, and 0.46±0.01 μmol h$^{-1}$, respectively. However, compared with that of the parent CALB-EF5, the $V_R$ values of the mutant lipases only decreased slightly (Table 1). As a result, the values of $V_R/V_S$ increased from 1.17 (the parent enzyme) to 29.78 (A281S), 46.71 (D223V), and 200.11 (D223V/A281S). Overall, it indicated that the decreases in the dynamics of the pocket and channel resulting from mutations at sites 223 and 281 led to a sharp decline in the initial generation rate of the S-enantiomer ($V_S$) and thereby increased R-enantioselectivity at 30° C. The mutant A282S exhibited similar initial generation rate in comparison to that of the parent enzyme.

TABLE 1

The formation rate of R and S enantiomers catalyzed by CALB mutants at 30° C.

| | Initial formation rate [μmol h$^{-1}$] | | |
|---|---|---|---|
| Mutants | $V_R$ | $V_S$ | $V_R/V_S$ |
| EF5 | 93.90 ± 4.35 | 79.99 ± 3.18 | 1.17 |
| A282S | 93.85 ± 5.54 | 78.98 ± 5.31 | 1.19 |
| A281S | 93.52 ± 8.02 | 3.14 ± 0.04 | 29.78 |
| D223V | 93.42 ± 2.35 | 2.00 ± 0.01 | 46.71 |
| D223V/A281S | 92.05 ± 4.82 | 0.46 ± 0.01 | 200.11 |
| W104A | 93.75 ± 5.35 | 75.23 ± 5.94 | 1.25 |
| Q157N | 94.00 ± 6.54 | 93.85 ± 5.54 | 1.00 |

Example 5: Measurement of Kinetic Parameters of the CALB Mutants

The kinetic parameters of the R/S-enantiomers, including $K_m$ and $k_{cat}$, were calculated by measuring the initial rates of product formation at different concentrations of R/S-enantiomers (1-20 mM) at 30° C. Samples were withdrawn, extracted, and analyzed by HPLC. All assays were carried out at least three times. The data were plotted, and $K_m$ and $k_{cat}$ values were obtained by the double reciprocal method.

The kinetic parameters of the CALB mutants were determined with optically pure R- and S-enantiomers as substrates, and the results were listed in Table 2. For the mutant D223V/A281S, the $k_{cat}$, $K_m$, and $k_{cat}/K_m$ values towards the R-enantiomer were 5.6% higher, 34% lower, and 58.2% higher, respectively, than those of the parent EF5 enzyme. The $k_{cat}$, $K_m$, and $k_{cat}/K_m$ values towards the S-enantiomer exhibited a 16.2% decrease, 88.1-fold increase, and 100-fold decrease, respectively, compared with the corresponding values in the parent EF5 enzyme.

TABLE 2

Kinetic parameters of CALB mutants

| | R-enantiomer | | | | S-enantiomer | | | |
| --- | --- | --- | --- | --- | --- | --- | --- | --- |
| Mutant | $k_{cat}$ [s$^{-1}$] | $K_m$ [mM] | $k_{cat}/K_m$ [mM$^{-1}$ s$^{-1}$] | Fold | $k_{cat}$ [s$^{-1}$] | $K_m$ [mM] | $k_{cat}/K_m$ [mM$^{-1}$ s$^{-1}$] | Fold |
| EF5 | 4.96 | 0.60 | 8.29 | 1.00 | 4.59 | 0.64 | 7.12 | 1.00 |
| A282S | 4.94 | 0.61 | 8.10 | 0.98 | 4.60 | 0.65 | 7.11 | 1.00 |
| A281S | 5.02 | 0.55 | 9.12 | 1.10 | 4.52 | 15.40 | 0.30 | 0.04 |
| D223V | 5.13 | 0.42 | 12.21 | 1.47 | 4.01 | 15.42 | 0.26 | 0.04 |
| D223V/A281S | 5.24 | 0.40 | 13.10 | 1.58 | 3.95 | 56.43 | 0.07 | 0.01 |
| W104A | 5.01 | 0.55 | 9.10 | 1.10 | 4.58 | 0.60 | 7.63 | 1.07 |
| Q157N | 4.98 | 0.58 | 8.59 | 1.04 | 4.61 | 0.52 | 8.87 | 1.25 |

Example 6: Determination of R-Ee Value and Conversion Rate of the CALB Mutants

The esterification reaction was carried out by immobilized EF5 or new mutants (80 g/L) in acetonitrile, containing 60 g/L 3-TBDMSO glutaric anhydride with methanol for 12 hr at 37° C. The activity of immobilized mutant enzymes was maintained at the same level. The concentrations of (R)-3-TBDMSO glutaric acid methyl monoester and enantioselectivity were determined by HPLC.

The R-ee of A281S/D223V was the highest, reaching 99%. The R-ee of A281S and D223V were 93.5% and 95.8%, respectively. The enantioselectivity of other mutants were shown in the Table 3 below.

TABLE 3

Production of R-enantiomers by CALB mutants

| Mutants | Temperature [° C.] | Time [h] | R-ee [%] | Conv. [%] | space-time yield [g · L$^{-1}$ · d$^{-1}$] |
| --- | --- | --- | --- | --- | --- |
| EF5 | 5 | 60 | 98.50 | 70.49 | 18.89 |
| EF5 | 37 | 12 | 8 | 82.17 | 110.11 |
| A282S | 37 | 12 | 8.32 | 82.10 | 110.01 |
| A281S | 37 | 12 | 93.50 | 81.23 | 108.85 |
| D223V | 37 | 12 | 95.80 | 79.75 | 106.87 |
| D223V/A281S | 37 | 12 | >99 | 80.25 | 107.54 |
| W104A | 37 | 12 | 10% | 78.33 | 104.96 |
| Q157N | 37 | 12 | 1% | 76.25 | 102.18 |

Example 7: Effects of Metal Ions on Enantioselectivity

The esterification reaction was carried out by immobilized EF5 or new mutants (80 g/L) in acetonitrile, containing 60 g/L 3-TBDMSO glutaric anhydride with methanol for 12 hr at 30° C. 0.5% v/v metal ion solution (2.4 M, MgCl$_2$, CaCl$_2$ LiCl, NaCl, BaCl$_2$ or KCl) was added to the system. The activity of immobilized mutant enzymes was maintained at the same level. The concentrations of (R)-3-TBDMSO glutaric acid methyl monoester and enantioselecitivity were determined by HPLC. The results indicated that MgCl$_2$ showed the greatest effect on R-ee, increased to 99%, and CaCl$_2$ and KCl showed slight effect, while LiCl, NaCl and BaCl$_2$ showed no effect.

Example 8: The Preparation of (R)-3-Substituted Glutaric Acid Monoesters

The esterification reaction was carried out by immobilized EF5 or new mutants (60 g/L) in acetonitrile, containing 60 g/L 3-TBDMSO glutaric anhydride with methanol for 12 hr at 37° C. 0.5% v/v metal ion solutions (MgCl$_2$ 2.4 M) were added to the system. The activity of immobilized mutant enzymes was maintained at the same level. The concentrations of (R)-3-TBDMSO glutaric acid methyl monoester and enantioselecitivity were determined by HPLC. The results indicated that the R-ee of A281S, D223V and A281S/D223V mutants reached 99%.

Example 9: The Preparation of (R)-3-Substituted Glutaric Acid Monoesters

The reaction was carried out by immobilized EF5 and new mutants (60 g/L) in acetonitrile, containing 60 g/L 3-TBDMSO glutaric anhydride with methanol for 30 hr at 20° C. 0.5% v/v metal ion solutions (MgCl$_2$ 2.4 M) were added to the system. The activity of immobilized mutant enzymes was maintained at the same level. The concentrations of (R)-3-TBDMSO glutaric acid methyl monoester and enantioselecitivity were determined by HPLC. The results indicated that the R-ee of A281S, D223V and A281S/D223V mutants reached 99%.

Example 10: The Preparation of (R)-3-Substituted Glutaric Acid Monoesters

The reaction was carried out by immobilized EF5 and new mutants (60 g/L) in acetonitrile, containing 60 g/L 3-TBDMSO glutaric anhydride with methanol for 8 hr at 55° C. 0.5% v/v metal ion solutions (MgCl$_2$ 2.4 M) were added to the system. The activity of immobilized mutant enzymes was maintained at the same level. The concentrations of (R)-3-TBDMSO glutaric acid methyl monoester and enantioselecitivity were determined by HPLC. The results indicated that the R-ee of A281S, D223V and A281S/D223V mutants reached 98.5%.

Example 11: The Preparation of (R)-3-Substituted Glutaric Acid Monoesters

The reaction was carried out by immobilized EF5 and new mutants (60 g/L) in acetonitrile, containing 60 g/L 3-TBDMSO glutaric anhydride with methanol for 2 hr at 70° C. 0.5% v/v metal ion solutions (MgCl$_2$ 2.4 M) were added to the system. The activity of immobilized mutant enzymes was maintained at the same level. The concentrations of (R)-3-TBDMSO glutaric acid methyl monoester and enantioselecitivity were determined by HPLC. The results indicated that the R-ee of A281S, D223V and A281S/D223V mutants reached 98%.

Example 12: The Preparation of (R)-3-Substituted Glutaric Acid Monoesters

The reaction was carried out by immobilized EF5 and new mutants (80 g/L) in acetonitrile, containing 60 g/L 3-TBDMSO glutaric anhydride with methanol for 48 hr at 5° C. 0.5% v/v metal ion solutions ($MgCl_2$ 2.4 M) were added to the system. The activity of immobilized mutant enzymes was maintained at the same level. The concentrations of (R)-3-TBDMSO glutaric acid methyl monoester and enantioselecitivity were determined by HPLC. The results indicated that the R-ee of A281S, D223V and A281S/D223V mutants reached 99%.

The above preferred embodiments are described for illustration only, and are not intended to limit the scope of the invention. It should be understood, for a person skilled in the art, that various improvements or variations can be made therein without departing from the spirit and scope of the invention, and these improvements or variations should be covered within the protecting scope of the invention.

What is claimed is:

1. A *candida antarctica* lipase B mutant, wherein said mutant lipase has one of the following amino acid substitutions: D223V, A281S, and D223V/A281S in the parent enzyme of SEQ ID NO:1.

2. The mutant of claim 1, wherein the amino acid sequence of said *candida antarctica* lipase B mutant is SEQ ID NO:15, SEQ ID NO:16 or SEQ ID NO:17.

3. The mutant of claim 1, wherein the nucleotide sequence encoding said mutant lipase is SEQ ID NO:2, SEQ ID NO:3 or SEQ ID NO:4.

4. A recombinant plasmid vector, wherein said recombinant plasmid vector comprises a nucleotide sequence encoding said mutant lipase of claim 1.

5. A method of producing (R)-3-substituted glutaric acid alkyl monoester compounds, comprising using said mutant lipase of claim 1 as a catalyst in an esterification reaction to make (R)-3-substituted glutaric acid alkyl monoester compounds.

6. The method of claim 5, comprising using said mutant lipase of claim 1 as a catalyst in an esterification reaction to make (R)-3-t-butyl-dimethyl-silyloxy glutaric acid methyl monoester.

7. The method of claim 5, comprising adding said mutant lipase of claim 1 to a substrate, a co-substrate, and an organic solvent to perform a non-aqueous phase esterification reaction, wherein said substrate is 3-substituted glutaric anhydride or 3-substituted glutaric acid and said co-substrate is organic alcohol, and wherein the molar ratio of said substrate to said co-substrate is 1:20-20:1, the mass ratio of said substrate to said mutant lipase is 1:6-6:1, and the molar ratio of said organic solvent to said substrate is 2:1-300:1.

8. The method of claim 7, further comprising adding 0.5% v/v metal ion solution to said esterification reaction, wherein said metal ion solution is $MgCl_2$, $CaCl_2$ or KCl.

9. The method of claim 8, wherein concentration of said mutant lipase of claim 1 is 1 to 100 g/L and concentration of said substrate is 10 to 300 g/L, and wherein said esterification reaction is performed at 5-70° C., 200-500 rpm for 2-48 hours.

* * * * *